United States Patent [19]

Lee

[11] 4,447,634

[45] May 8, 1984

[54] HERBICIDAL ARYLSULFONAMIDE DERIVATIVES OF PHENOXYBENZOIC ACIDS

[75] Inventor: Guang-Huei Lee, East Windsor, N.J.

[73] Assignee: Rhone-Poulenc Agrochimie, Lyons, France

[21] Appl. No.: 259,336

[22] Filed: Apr. 30, 1981

[51] Int. Cl.$^3$ .................. A01N 41/06; C07C 143/78; C07C 143/82
[52] U.S. Cl. ................ 560/13; 260/465 D; 564/87; 564/89; 564/91; 71/103
[58] Field of Search ............. 564/87, 89, 91; 260/465 D; 560/12, 13

[56] References Cited

U.S. PATENT DOCUMENTS

| | | | |
|---|---|---|---|
| 3,317,540 | 5/1967 | Wakeman et al. | 564/91 X |
| 3,622,626 | 11/1971 | Moore | 71/103 X |
| 3,641,114 | 2/1972 | Childress et al. | 564/91 X |
| 3,663,615 | 5/1972 | Ziegler et al. | 564/91 X |
| 3,906,024 | 9/1975 | Moore et al. | 71/103 X |
| 4,063,929 | 12/1977 | Bayer et al. | 71/115 |
| 4,285,723 | 8/1981 | Cartwright et al. | 71/103 |

*Primary Examiner*—Thomas A. Waltz
*Attorney, Agent, or Firm*—Morgan, Finnegan, Pine, Foley & Lee

[57] ABSTRACT

There is provided herbicidal arylsulfonamide derivatives of phenoxybenzoic acids. These compounds are particularly useful when applied in a post-emergence application to soybean fields containing broadleaf weeds.

14 Claims, No Drawings

HERBICIDAL ARYLSULFONAMIDE DERIVATIVES OF PHENOXYBENZOIC ACIDS

BACKGROUND OF THE INVENTION

The invention is concerned with herbicidal arylsulfonamide derivatives of phenoxybenzoic acids.

The compound, 5-[2-chloro-4-(trifluoromethyl) phenoxy]-2-nitrobenzoic acid, including the salt forms thereof, is known to have herbicidal activity. According to a particular herbicidal treatment, it has been proposed to apply this compound in a post-emergence fashion to control weeds, especially broadleaf weeds, in soybean fields. Accordingly, in such an application, a herbicide must possess the following two properties at the applied dosage rate: (1) the ability to control the target weeds; and (2) the ability to remain safe to the soybeans.

In attempting to improve on the herbicidal properties of 5-[2-chloro-4-(trifluoromethyl)phenoxy]-2-nitrobenzoic acid and salts thereof, various derivatives of these compounds have been proposed including alkyl and cycloalkyl esters, alkylthio esters, phenyl ester, alkyl and dialkyl amido and benzyl chloride forms. U.S. Patents which describe such compounds and the like include U.S. Pat. Nos. 3,652,645; 3,784,635; 3,873,302; 3,983,168; 3,907,866; 3,798,276; 3,928,416; and 4,063,929. European Pat. No. 3416 to Imperial Chemical Industries Limited describes various alkylsulfonamide derivatives of phenoxybenzoic acids. For example, the simple methyl ester of the above-mentioned acid, i.e., methyl 5-[2-chloro-4-(trifluoromethyl)-phenoxy]-2-nitrobenzoate, has been proposed, and it has been discovered that this compound has even greater herbicidal activity than 5-[2-chloro-4-(trifluoromethyl)-phenoxy]-2-nitrobenzoic acid with respect to various weeds, e.g., broadleaf weeds. However, it has also been discovered that methyl 5-[2-chloro-4-(trifluoromethyl)-phenoxy]-2-nitrobenzoate has a relatively large degree of post-emergence herbicidal activity with respect to crops such as soybeans.

Accordingly, there is a need in the art for compounds which have a desirable combination of herbicidal properties with respect to weed activity and crop safety.

SUMMARY OF THE INVENTION

This invention provides certain herbicidal compounds of the formula:

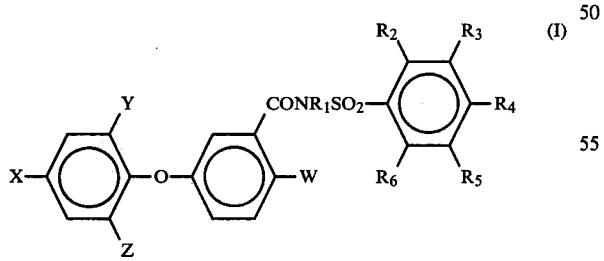

where W, X, Y, Z, $R_1$, $R_2$, $R_3$, $R_4$, $R_5$ and $R_6$ represent groups capable of being incorporated into the compound of Formula (I), and which, in combination, impart herbicidal activity thereto, expressly provided that $R_2$ and/or $R_6$ shall not be COOH or salts of COOH (e.g., COONa).

Preferably, the groups W, X, Y, Z, $R_1$, $R_2$, $R_3$, $R_4$, $R_5$ and $R_6$ are selected as follows:

(1) W is selected from the group consisting of halo (e.g., F, Cl, Br or I), $NO_2$, CN and H;

(2) X is selected from the group consisting of halo (e.g., F, Cl, Br or I) and halo-substituted $C_1$–$C_4$ alkyl (e.g., $CF_3$, $HCF_2$, etc.);

(3) Y is selected from the group consisting of halo (e.g., F, Cl, Br or I), $CF_3$, CN and $NO_2$;

(4) Z is selected from the group consisting of halo (e.g., F, Cl, Br or I) and H;

(5) $R_1$ is selected from the group consisting of H, $C_1$–$C_6$ alkyl, alkali metal salt (e.g., Na or K salt), ammonium salt and quaternary ammonium salt; and (6) $R_2$, $R_3$, $R_4$, $R_5$ and $R_6$ are the same or different and are selected from the group consisting of halo (e.g., F, Cl, Br or I), alkyl (e.g., $C_1$–$C_6$ alkyl), H, $NO_2$, $CO_2R_7$, CN, $OR_8$, $CF_3$ and substituted alkyl (e.g., $C_1$–$C_4$ alkyl substituted with one or more groups selected from the group consisting of Cl, $NO_2$, $C_1$–$C_4$ alkoxy and $C_1$–$C_4$ alkyl esters of COOH), where $R_7$ and $R_8$ are the same or different and are $C_1$–$C_6$ alkyl.

Preferably, the groups W, X, Y and Z are selected such that the compounds of Formula I correspond to the formula:

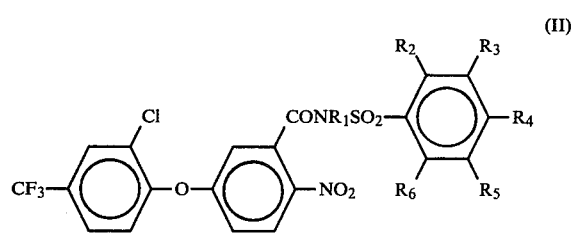

The compounds of Formulae I and II may be prepared, e.g., by methods set forth by way of example as follows.

EXAMPLE 1

Preparation of 5-(2-chloro-4-trifluoromethylphenoxy)-2-nitro-N-para-toluenesulfonylbenzamide (Compound 1).

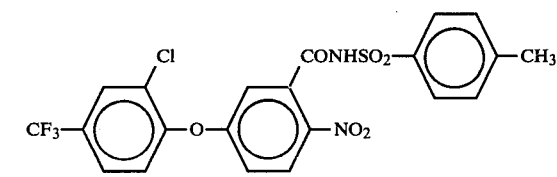

A catalyst amount (ca. 10 gm) of N,N-dimethylaminopyridine (available from the Aldrich Chemical Co. Ltd.) was added to a stirred mixture of 5-(2-chloro-4-trifluoromethylphenoxy)-2-nitrobenzoic acid (260 gm, 0.72 moles) in 350 ml toluene under nitrogen. A solution of para-toluenesulfonylisocyanate (available from the Aldrich Chemical Co., Ltd., 180 gm, 0.94 moles) in toluene (150 ml) was then added dropwise to the above solution with stirring. After the addition was complete the mixture was brought to reflux for six hours. Toluene in the cooled solution was then removed in vacuo. The resulting waxy solid was further recrystalized from toluene to yield 170 gm (0.33 moles, 46%,) of the desired product.

NMR (CD$_3$COCD$_3$), δ (ppm): 2.55 (S.3H, CH$_3$-Aryl; 7.30–8.50); (m. 10H. Aryl protons): IR (KBr, cm$^{-1}$) 3205, 1705, 1580; m.p. 150° C.

EXAMPLE 2

Alternate preparation of compound 1.

A solution of triethylamine (0.60 gm, 5.9 mmoles) and N,N-Dimethylaminopyridine (available from the Aldrich Chemical Co., Ltd.), catalytic amount, ca. 5 mg, in THF (15 ml) was added dropwise to a stirred THF (25 ml) solution containing 5-(2-chloro-4-trifluoromethylphenoxy)-2-nitrobenzoyl chloride (1.80 gm, 4.7 mmoles) and p-toluenesulfonamide, (available from the Aldrich Chemical Co., Ltd., 1.00 gm, 5.8 mmoles) at room temp. Stirring was continued overnight and the solution was filtered, concentrated to give a brown oil. The brown oil was purified by medium pressure liquid chromatography (silica, 5% acetic acid in chloroform) followed by recrystallization to yield 1.10 gm purified (43%) product. m.p. 156°–157° C. N.M.R. & I.R. data were the same as in Example 1.

In a similar manner, the following compounds were prepared according to the formula (III)

| Compound | X | R$_1$ | R$_2$ | R$_3$ | R$_4$ | R$_5$ | R$_6$ | m.p. °C. |
|---|---|---|---|---|---|---|---|---|
| 2 | CF$_3$ | Na | H | H | CH$_3$ | H | H | — |
| 3 | CF$_3$ | H | H | H | Cl | H | H | 176-8 |
| 4 | CF$_3$ | H | H | H | H | H | H | 135-8.5 |
| 5 | Cl | H | H | H | CH$_3$ | H | H | 159-61 |
| 6 | Cl | H | H | H | Cl | H | H | 158-64 |
| 7 | Cl | H | H | H | H | H | H | 181-3 |
| 8 | CF$_3$ | CH$_3$ | H | H | CH$_3$ | H | H | — |
| 9 | CF$_3$ | NH$_4$ | H | H | Cl | H | H | — |
| 10 | CF$_3$ | NH$_4$ | H | H | CH$_3$ | H | H | — |
| 11 | Cl | NH$_4$ | H | H | Cl | H | H | — |
| 12 | CF$_3$ | H | CO$_2$CH$_3$ | H | H | H | H | — |

The compounds of this invention can be applied in various ways to achieve herbicidal action. They can be applied per se, as solids or in vaporized form, but are preferably applied as the toxic components in pesticidal compositions of the compound and a carrier. These compositions are preferably applied directly to the soil and often incorporated therewith. The compositions can be applied as granulars or dusts; as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers include water, organic solvents such as alcohols, ketones, light oils, and medium oils and vegetable oils such as cottonseed oil.

In practice, herbicidal application is measured in terms of pounds of herbicide applied per acre. The compounds of this invention are effective herbicides when applied in herbicidal amounts, i.e., at rates between about 0.03 pound and about 10 pounds per acre.

HERBICIDAL EFFECTIVENESS

Method of Propagating Test Species

Crop and weed species are planted in 8"×10" disposable fiber flats containing potting soil to provide each flat with a 4" row of all test species. Crop species consist of field corn (CN), cotton (CT), and soybeans (SB). The weed species consist of foxtail millet (FM), green foxtail (GF), velvetleaf (VL), cocklebur (CB), wild mustard (WM) and pigweed (PW).

Cotton, corn, soybean, and cocklebur plantings consist of 4 to 5 seeds per row depending upon species. The smaller seeded species (velvetleaf, wild mustard, pigweed, foxtail millet and green foxtail) are planted in an uncounted but sufficient number to provide a solid row of seedlings.

Plantings for the pre- and post-emergence portions of the test are identical as to seeding. The initial watering until emergence is done from the top. The post-emergence phase is propagated in advance so as to provide plants of the proper stage of development at the time of treatment. Plantings for the pre-emergence phase are made not more than one day in advance of treatment.

The desired stage of development for treatment of the post-emergence broadleaf species (CT, SB, CB, VL, WM, PW) is the one true leaf or first trifoliate leaf stage. The desired stage for corn would be a height of 3-4", while a 2" height would be adequate for the grasses.

Method of Treatment

Spray applications are made with a handgun sprayer (aspirator type) simultaneously to one flat of established plants for the post-emergence phase and one newly seeded flat for the pre-emergence phase. A 10 lb./acre treatment rate consists of the uniform application of 116 milligrams of test compound to the combined area of the two flats (160 sq. inches). Application is made in a solvent mixture consisting of 40 ml acetone and 40 ml water and a surfactant concentration of 0.1 percent.

Following spray application, flats are returned to the greenhouse where watering of the post-emergence phase is done only by subirrigation. The pre-emergence phase is top watered by sprinkling until after test species have emerged. Subsequent watering is by subirrigation.

Two weeks after treatment, the pre- and post-emergence injury and control is rated on a 0–100 percent injury and control scale. Special physiological effects are rated as to intensity also at this time.

The following lists the metric equivalents for rates expressed as lb./acre.

| Application Rate | |
|---|---|
| US - lb./acre | Metric - kg/ha |
| 10.0 | 11.2 |
| 4.0 | 4.48 |
| 2.0 | 2.24 |
| 1.0 | 1.12 |
| 0.5 | 0.56 |
| 0.25 | 0.28 |
| 0.125 | 0.14 |
| 0.0625 | 0.07 |

Pre-emergence test results are set forth in Table I and post-emergence test results are set forth in Table II.

TABLE I

| Compound No. | Dosage Lbs./Acre | Pre-Emergence | | | | | | | | |
|---|---|---|---|---|---|---|---|---|---|---|
| | | FM | GF | VL | CB | WM | PW | CT | CN | SB |
| 1 | 2 | 100 | 90 | 80 | 0 | 100 | 100 | 10 | 10 | — |
| | 1 | 100 | 90 | 70 | 0 | 100 | 90 | 30 | 0 | — |
| | ½ | 90 | 90 | 60 | 0 | 100 | 80 | 10 | 0 | — |
| | ¼ | 80 | 60 | 10 | 0 | 90 | 70 | 20 | 0 | — |
| 2 | 4 | 90 | 90 | 80 | 70 | 100 | 100 | 50 | 40 | — |
| | 2 | 90 | 50 | 40 | 70 | 90 | 90 | 0 | 20 | — |
| | 1 | 90 | 50 | 30 | 10 | 100 | 90 | 10 | 10 | 20 |
| | ½ | 70 | 10 | 40 | 0 | 90 | 60 | 0 | 20 | 0 |
| | ¼ | 40 | 10 | 20 | 0 | 90 | 70 | 10 | 10 | 0 |
| 3 | 1 | — | 50 | 0 | 70 | 0 | 70 | 20 | 0 | 10 |
| | ¼ | — | 10 | 0 | — | 0 | 50 | 20 | 0 | 10 |
| 4 | 1 | — | 20 | 0 | 0 | 70 | 60 | 20 | 30 | 0 |
| | ¼ | — | 0 | 0 | — | 0 | 30 | 0 | 0 | 1 |
| 5 | 2 | — | 40 | 20 | 30 | 10 | 50 | 20 | 20 | 0 |
| | ½ | — | 10 | 0 | — | 0 | 10 | 10 | 0 | 2 |
| 6 | 2 | — | 30 | 0 | 30 | 0 | 20 | 0 | 10 | 0 |
| | ½ | — | 20 | 30 | 0 | 0 | 0 | 10 | 0 | 0 |
| 7 | 2 | — | 30 | 10 | 0 | 0 | 10 | 0 | 0 | 0 |
| | ½ | — | 20 | 60 | — | 0 | 50 | 10 | 0 | 0 |
| 8 | 1 | — | 50 | 0 | 100 | 0 | 30 | 20 | 0 | 0 |
| | ¼ | — | 10 | 20 | — | 0 | 0 | 0 | 10 | 10 |
| 9 | 1 | — | 0 | 70 | 0 | 90 | 90 | 20 | 0 | 50 |
| | ¼ | — | 0 | 60 | 0 | 50 | 90 | 0 | 0 | 0 |
| 10 | 1 | — | 0 | 30 | 100 | 90 | 100 | 20 | 20 | 30 |
| | ¼ | — | 0 | 0 | 0 | 70 | 80 | 10 | 0 | 30 |
| 11 | ¼ | — | 0 | 0 | 50 | 10 | 60 | 20 | 0 | 10 |
| 12 | 2 | 70 | 60 | 100 | 20 | 100 | 100 | 20 | 10 | 0 |
| | 1 | 30 | 30 | 90 | 10 | 90 | 100 | 20 | 10 | 0 |
| | ½ | 20 | 20 | 70 | 0 | 90 | 100 | 0 | 0 | 0 |
| | ¼ | 0 | 0 | 70 | 0 | 90 | 80 | 0 | 0 | 0 |
| | ⅛ | — | 20 | 30 | 60 | 40 | 80 | 0 | 0 | 0 |
| | 1/16 | — | 20 | 20 | 40 | 40 | 70 | 0 | 0 | 30 |

TABLE II

| Compound No. | Dosage Lbs./Acre | Post-Emergence | | | | | | | | |
|---|---|---|---|---|---|---|---|---|---|---|
| | | FM | GF | VL | CB | WM | PW | CT | CN | SB |
| 1 | 2 | — | 100 | 100 | 100 | 100 | 100 | 100 | 80 | 70 |
| | 1 | — | 90 | 100 | 90 | 100 | 100 | 100 | 40 | 50 |
| | ½ | — | 90 | 100 | 80 | 100 | 100 | 90 | 20 | 40 |
| | ¼ | — | 70 | 90 | 60 | 100 | 100 | 70 | 10 | 10 |
| | ⅛ | 60 | 40 | 20 | 70 | 90 | 80 | 40 | 10 | 10 |
| | 1/16 | 40 | 30 | 30 | 70 | 80 | 80 | 40 | 0 | 0 |
| 2 | 4 | 100 | 100 | 100 | 100 | 100 | 100 | 100 | 90 | 40 |
| | 2 | 100 | 100 | 100 | 80 | 100 | 100 | 90 | 90 | 40 |
| | 1 | 80 | 70 | 60 | 80 | 100 | 100 | 60 | 40 | 20 |
| | ½ | 70 | 60 | 40 | 70 | 90 | 100 | 70 | 30 | 30 |
| | ¼ | 20 | 30 | 30 | 60 | 80 | 100 | 60 | 30 | 20 |
| 3 | 1 | — | 30 | 80 | 90 | 100 | 100 | 80 | 60 | 30 |
| | ¼ | — | 60 | 60 | 70 | 70 | 100 | 70 | 50 | 10 |
| | ⅛ | — | 10 | 10 | 40 | 90 | 100 | 40 | 10 | 10 |
| | 1/16 | — | 10 | 10 | 70 | 70 | 100 | 30 | 30 | 10 |
| 4 | 1 | — | 50 | 30 | 100 | 100 | 100 | 70 | 50 | 10 |
| | ¼ | — | 40 | 30 | 60 | 80 | 100 | 60 | 60 | 10 |
| | ⅛ | — | 10 | 10 | 30 | 90 | 100 | 30 | 40 | 10 |
| | 1/16 | — | 10 | 0 | 20 | 80 | 100 | 30 | 30 | 10 |
| 5 | 2 | — | 30 | 80 | 30 | 90 | 100 | 50 | 40 | 40 |
| | ½ | — | 40 | 70 | 70 | 70 | 100 | 70 | 30 | 20 |
| 6 | 2 | — | 20 | 30 | 60 | 90 | 100 | 40 | 40 | 40 |
| | ½ | — | 30 | 20 | 60 | 80 | 100 | 40 | 40 | 30 |
| 7 | 2 | — | 30 | 70 | 70 | 100 | 100 | 70 | 10 | 30 |
| | ½ | — | 10 | 40 | 60 | 80 | 90 | 40 | 30 | 20 |
| 8 | 1 | — | 40 | 70 | 30 | 70 | 90 | 50 | 20 | 30 |
| | ¼ | — | 30 | 40 | 30 | 70 | 90 | 20 | 20 | 40 |
| 9 | 1 | 20 | 20 | 70 | 70 | 60 | 100 | 60 | 10 | 20 |
| | ¼ | 10 | 10 | 40 | 70 | 40 | 80 | 40 | 0 | 10 |
| 10 | 1 | 30 | 20 | 80 | 70 | 90 | 100 | 40 | 0 | 10 |
| | ¼ | 0 | 0 | 20 | 60 | 60 | 90 | 60 | 0 | 10 |
| 11 | ¼ | 10 | 0 | 20 | 40 | 40 | 40 | 20 | 0 | 10 |
| 12 | 2 | 90 | 80 | 100 | 100 | 100 | 100 | 80 | 80 | 30 |
| | 1 | 80 | 70 | 100 | 100 | 100 | 100 | 90 | 70 | 60 |
| | ½ | 70 | 70 | 100 | 90 | 100 | 100 | 70 | 50 | 30 |
| | ¼ | 70 | 40 | 90 | 70 | 80 | 90 | 70 | 30 | 10 |

By way of comparison, pre-emergence test results are set forth in Table III and post-emergence test results are

TABLE III

| X | R₁ | R₂ | R₃ | R₄ | R₅ | R₆ | Dosage Lbs./Acre | Pre-Emergence | | | | | | | | |
|---|---|---|---|---|---|---|---|---|---|---|---|---|---|---|---|---|
| | | | | | | | | FM | GF | VL | CB | WM | PW | CT | CN | SB |
| CF₃ | H | CO₂H | H | H | H | H | 2 | 30 | 30 | 40 | 0 | 60 | 90 | 0 | 20 | 20 |
| | | | | | | | 1 | 50 | 30 | 0 | 0 | 80 | 70 | 20 | 10 | 40 |
| | | | | | | | ½ | 50 | 20 | 30 | 0 | 40 | 30 | 40 | 30 | 40 |
| | | | | | | | ¼ | 20 | 10 | 0 | 70 | 40 | 20 | 30 | 0 | 10 |
| CF₃ | Na | CO₂Na | H | H | H | H | 2 | 30 | 30 | 0 | 30 | 50 | 60 | 0 | 0 | 0 |
| | | | | | | | 1 | 20 | 0 | 20 | 20 | 70 | 40 | 0 | 0 | 0 |
| | | | | | | | ½ | 0 | 20 | — | 70 | 1 | 40 | 0 | 10 | 20 |
| | | | | | | | ¼ | 0 | 0 | 0 | 0 | 0 | 30 | 10 | 0 | 0 |

TABLE IV

| X | R₁ | R₂ | R₃ | R₄ | R₅ | R₆ | Dosage Lbs./Acre | Post-Emergence | | | | | | | | |
|---|---|---|---|---|---|---|---|---|---|---|---|---|---|---|---|---|
| | | | | | | | | FM | GF | VL | CB | WM | PW | CT | CN | SB |
| CF₃ | H | CO₂H | H | H | H | H | 2 | 30 | 0 | 10 | 0 | 90 | 100 | 0 | 20 | 10 |
| | | | | | | | 1 | 30 | 20 | 10 | 0 | 60 | 40 | 0 | 20 | 10 |
| | | | | | | | ½ | 0 | 0 | 10 | 10 | 60 | 40 | 0 | 10 | 10 |
| | | | | | | | ¼ | 20 | 20 | 0 | 0 | 20 | 20 | 0 | 20 | 10 |
| CF₃ | Na | CO₂Na | H | H | H | H | 2 | 10 | 0 | 0 | 0 | 70 | 70 | 0 | 20 | 0 |
| | | | | | | | 1 | 30 | 30 | 10 | 0 | 60 | 20 | 40 | 10 | 0 |
| | | | | | | | ½ | 0 | 0 | 0 | 0 | 40 | 20 | 10 | 10 | 10 |
| | | | | | | | ¼ | 30 | 30 | 10 | 10 | 40 | 10 | 0 | 10 | 10 |

The compounds of the present invention may be particularly advantageous when used to control weeds in field of crops which are relatively tolerant thereto. For instance, the foregoing data demonstrates that certain crop species are more tolerant to these compounds than certain grass or broadleaf weed species. The herbicidal compounds of the present invention are particularly useful when applied in post-emergence applications to control broadleaf weeds, e.g., velvetleaf, cocklebur, wild mustard and pigweed, in soybean fields.

Although the present invention has been described with preferred embodiments, it is to be understood that modifications and variations may be restored to, without departing from the spirit and scope of this invention, as those skilled in the art will readily understand. Such modifications and variations are considered to be within the purview and scope of the appended claims.

What is claimed is:

1. A herbicidal compound of the formula

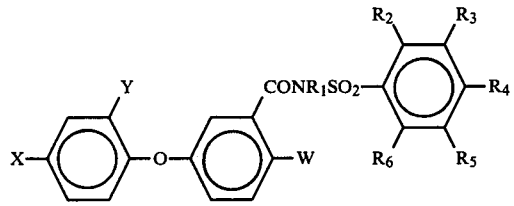

wherein W, X, Y, Z, R₁, R₂, R₃, R₄, R₅ and R₆ are as follows:

(1) W is selected from the group consisting of halo, NO₂, CN and H;

(2) X is selected from the group consisting of halo and halo-substituted $C_1$-$C_4$ alkyl;

(3) Y is selected from the group consisting of halo, CF₃, CN and NO₂;

(4) Z is selected from the group consisting of halo and H;

(5) R₁ is selected from the group consisting of H, $C_1$-$C_6$ alkyl, alkali metal salt, ammonium salt and quarternary ammonium salt; and (6) R₂, R₃, R₄, R₅ and R₆ are the same or different and are selected from the group consisting of halo, alkyl, H, NO₂, CO₂R₇, CN, OR₈, CF₃ and substituted alkyl, wherein R₇ and R₈ are the same of different and are $C_1$-$C_6$ alkyl.

2. A herbicidal compound according to claim 1 of the formula

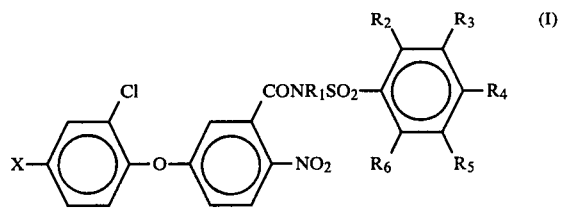

wherein X is CF₃ or Cl.

3. A herbicidal compound according to claim 2 where:
X is CF₃;
R₄ is CH₃; and
R₁, R₂, R₃, R₅ and R₆ are H.

4. A herbicidal compound according to claim 2 where:
X is CF₃;
R₁ is Na;
R₄ is CH₃; and
R₂, R₃, R₅ and R₆ are H.

5. A herbicidal compound according to claim 2 where:
X is CF₃;
R₄ is Cl; and
R₁, R₂, R₃, R₅ and R₆ are H.

6. A herbicidal compound according to claim 2 where:
X is CF₃; and
R₁, R₂, R₃, R₄, R₅ and R₆ are H.

7. A herbicidal compound according to claim 2 where:
X is Cl;
R₄ is CH₃; and $R_1$, $R_2$, $R_3$, $R_5$ and $R_6$ are H.

8. A herbicidal compound according to claim 2 where:
X is Cl;
$R_4$ is Cl; and
$R_1$, $R_2$, $R_3$, $R_5$ and $R_6$ are H.

9. A herbicidal compound according to claim 2 where:
X is Cl; and
$R_1$, $R_2$, $R_3$, $R_4$, $R_5$ and $R_6$ are H.

10. A herbicidal compound according to claim 2 where:
X is $CF_3$;
$R_1$ is $CH_3$;
$R_4$ is $CH_3$; and
$R_2$, $R_3$, $R_5$ and $R_6$ are H.

11. A herbicidal compound according to claim 2 where:
X is $CF_3$;
$R_1$ is $NH_4$;
$R_4$ is Cl; and
$R_2$, $R_3$, $R_5$ and $R_6$ are H.

12. A herbicidal compound according to claim 2 where:
X is $CF_3$;
$R_1$ is $NH_4$;
$R_4$ is $CH_3$; and
$R_2$, $R_3$, $R_5$ and $R_6$ are H.

13. A herbicidal compound according to claim 2 where:
X is Cl;
$R_1$ is $NH_4$;
$R_4$ is Cl; and
$R_2$, $R_3$, $R_5$ and $R_6$ are H.

14. A herbicidal compound according to claim 2 where:
X is $CF_3$;
$R_2$ is $CO_2CH_3$; and
$R_1$, $R_3$, $R_4$, $R_5$ and $R_6$ are H.

* * * * *